United States Patent [19]

Barbier et al.

[11] Patent Number: 5,204,099

[45] Date of Patent: Apr. 20, 1993

[54] COSMETIC COMPOSITION CONTAINING AMINO ACID COPOLYMERS WHICH IS USEFUL AS A MOISTURIZER

[75] Inventors: Alain Barbier, Saint Clement la Riviere; Joseph Millan, Juvignac; Michel Sabadie, Bernay, all of France

[73] Assignee: Sanofi, Paris, France

[21] Appl. No.: 654,187

[22] Filed: Feb. 12, 1991

[30] Foreign Application Priority Data

Feb. 12, 1990 [FR] France .................. 90 01618

[51] Int. Cl.$^5$ .............................................. A61K 7/00
[52] U.S. Cl. ..................... 424/401; 424/70; 424/71; 514/18; 514/773; 514/801; 514/873; 528/310; 528/328; 530/324; 530/325; 530/326; 530/327; 530/328; 530/329; 530/330
[58] Field of Search ............... 424/401, 70, 71; 514/18, 773, 801, 873; 530/330, 324, 325, 326, 327, 328, 329; 528/310, 328

[56] References Cited

U.S. PATENT DOCUMENTS

| | | | |
|---|---|---|---|
| 3,076,790 | 2/1963 | Fox et al. | 528/313 |
| 4,590,260 | 5/1986 | Harada et al. | 528/328 |
| 4,594,409 | 6/1986 | Hayashi et al. | 528/328 |
| 4,696,981 | 9/1987 | Harada et al. | 522/176 |
| 4,745,161 | 5/1988 | Saudek et al. | 525/420 |
| 4,996,292 | 2/1991 | Fox et al. | 528/328 |

FOREIGN PATENT DOCUMENTS

| | | |
|---|---|---|
| 0142231 | 8/1984 | European Pat. Off. . |
| 0305282 | 8/1988 | European Pat. Off. . |
| 62-121728 | 6/1987 | Japan . |

OTHER PUBLICATIONS

Mansbridge, Arch. Dermatol. Rev., 279:465-69 (1987).
J. Am. Chem. Soc., 78:941-46 (1956).
Sci. Report of Toyo Soda, 29(1):37-54 (1985).
D. Lecaucheux and R. Panaras, Carbohydrate Polymers, 5:423-440 (1985).
D. Wilson, Int. J. Cosmet. Sci., 10:201-211 (1988).
Metzler et al., "Limited Sampling . . . NMR Data," Biochemistry, 28 (17), pp. 7045-7052, (1989).

Primary Examiner—Thurman K. Page
Assistant Examiner—Robert H. Harrison
Attorney, Agent, or Firm—Foley & Lardner

[57] ABSTRACT

The invention relates to the cosmetic use of an amino acid copolymer of the statistical formula

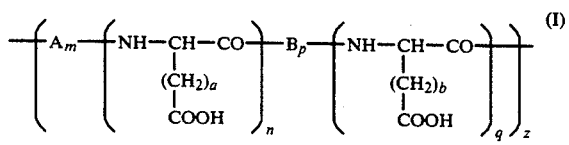

in which:
a and b are each independently 1 or 2;
A and B are similar or different and are an amino acid selected from: arginine, serine, proline, glycine, histidine, alanine, lysine, ornithine, citrulline, urocanic acid, asparagine or tyrosine;
m, n, p and q are integers such that the ratio $(n+q)/(m+p)$ is between 0.5 and 4; and
z is an integer such that the average molecular weight is between 1000 and 100,000; and/or one of its salts.

Application: cosmetic products.

10 Claims, No Drawings

COSMETIC COMPOSITION CONTAINING AMINO ACID COPOLYMERS WHICH IS USEFUL AS A MOISTURIZER

The present invention relates to the use of certain amino acid copolymers as moisturizers and to the cosmetic compositions in which said amino acid copolymers are present.

In the description of the present invention and in the claims which follow, the abbreviations used for the amino acids are those recommended by IUPAC.

It is known from the French patent applications published under no. 2 609 393 and 2 540 381 to use peptide compounds of natural origin for preparing pharmaceutical, dermatological or cosmetic compositions. It is also known from Japanese patent application 59-209635 to use polyglutamic acid as a moisturizer in shampoos, lotions or creams.

However, the action of polyglutamic acid or that of other mixtures of amino acid polymers tested hitherto is very transitory, which reduces the value of using them in cosmetic compositions for moisturizing the skin.

It has now been found that certain amino acid copolymers can be used for their durable moisturizing properties.

The present invention relates to cosmetic compositions containing one or more amino acid copolymers, said copolymers having substantial and persistent moisturizing properties. Furthermore, said copolymers are perfectly tolerated by the skin.

According to the present invention, an amino acid polymer or copolymer is understood as meaning a compound comprising an amino acid chain with an average molecular weight (MW) of between 1000 and 100,000.

The amino acid copolymers used as active ingredients in the cosmetic compositions according to the present invention are prepared by the copolymerization of 2, 3 or 4 amino acids which include at least one amino acid carrying an acid group on its side chain, namely glutamic acid or aspartic acid, the other amino acid or the other 2 amino acids being selected from the constituent amino acids of filaggrin and/or natural moisturizing factor (NMF). The amino acids resulting from the decomposition of filaggrin are described by MANSBRIGE in Arch. Dermatol. Rev., 1987, 279, 465-469. The composition of NMF is described in Labo. Pharma. Problèmes et Techniques, 1973, 273, 82.

Thus, according to the present invention, glutamic acid and/or aspartic acid form a copolymer with one other amino acid or, if appropriate, 2 other amino acids, said amino acids being selected from the following: arginine, serine, proline, glycine, histidine, alanine, lysine, ornithine, citrulline, urocanic acid, asparagine or tyrosine.

In its formula, the copolymer statistically contains a proportion of glutamic acid or aspartic acid, or else both glutamic acid and aspartic acid, of between 0.5 and 4 molar with respect to the other amino acid or the other two amino acids with which they form the copolymer.

Said copolymer, whose use as a moisturizer is a subject of the present invention, can be represented by the following statistical general formula:

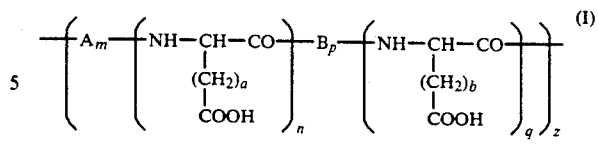

in which:
a and b are each independently 1 or 2;
A and B are similar or different and are an amino acid selected from: arginine, serine, proline, glycine, histidine, alanine, lysine, ornithine, citrulline, urocanic acid, asparagine or tyrosine;
m, n, p and q are integers such that the ratio $(n+q)/(m+p)$ is between 0.5 and 4; and
z is an integer such that the average molecular weight is between 1000 and 100,000;

The salts of said copolymer with mineral and organic bases compatible with cosmetological use are also within the scope of the present invention.

It will be noted that formula I is a statistical formula, i.e. the amino acid chains indicated are arbitrary and can be presented in any other combinations.

The cosmetic compositions according to the present invention contain from 0.1 to 10% by weight of a copolymer of formula (I) or a mixture of at least 2 copolymers of formula (I) in a cosmetic excipient.

Preferably, a cosmetic composition according to the invention contains from 0.5 to 5% by weight of a copolymer or a mixture of 2 copolymers (I) in a cosmetic excipient.

Each of the amino acids selected from arginine, serine, proline, glycine, histidine, alanine, lysine, ornithine, citrulline, urocanic acid, asparagine or tyrosine can form a copolymer (I) with glutamic acid and/or aspartic acid and thus produce a compound having moisturizing properties for the skin, said properties being durable.

When a mixture of 2 copolymers (I) is used, the glutamic acid and/or the aspartic acid is copolymerized with different amino acids A and, if appropriate, B.

The speed with which the moisturizing power of the copolymer (I) appears, and the period for which this moisturizing power persists, can vary with the amino acid chosen.

Thus, by suitably choosing a mixture of 2 copolymers (I), it is possible to prepare a cosmetic composition according to the invention whose moisturizing power is both quick to appear and durable, for example 30 minutes after application and for a period of time equal to at least 24 hours.

Thus, preferably, the cosmetic compositions according to the invention contain a mixture of 2 copolymers (I).

The copolymer (I) present as active ingredient in a cosmetic composition according to the invention preferably contains glutamic acid in a molar proportion of 0.5 to 4; this corresponds to the following values of the coefficients in statistical general formula (I): $a=b=2$ and $(n+q)/(m+p)$ is between 0.5 and 4. More particularly, the glutamic acid is in a molar ratio with only one other amino acid, in which case the values of the coefficients in the statistical formula of the copolymer (I) are:

$A=B$, $a=b=2$ and $(n+q)/(m+p)=1$.

Finally, the cosmetic composition according to the invention most preferably contains a copolymer selected from Lys-Glu (1/1) and Pro-Glu (1/1) or, preferably, a mixture of these 2 copolymers.

The amino acid copolymers (I) are known or are prepared by known methods.

The amino acids activated or not and protected, if necessary, on their side group polymerize in the presence of a basic initiator, for example a secondary amine or a tertiary amine such as triethylamine. The reaction is carried out in a solvent in which the monomer and the polymer are soluble, for example dichloromethane, dimethylformamide, dimethylsulfoxide or dioxane (J. Am. Chem. Soc., 1956, 78, 941–946). The polymerization may be performed starting from the N-carboxyanhydride of the amino acid, prepared according to H. Leuchs (Ber. Dtsch. Chem. Ges., 1906, 39, 857). This method can also be applied to the preparation of a copolymer of 2 or 3 different amino acids.

The polymerization reaction can also be carried out by reacting an initiator with amino acids in the form of activated esters.

The copolymers obtained in this way have statistical distributions of the amino acids and an average molecular weight within the range between 1000 and 100.000.

If it is desired to obtain polymers in which the distribution of the amino acids is regular in a sequence, conventional methods of peptide synthesis can be used to prepare the polypeptide segments corresponding to the desired chain, the corresponding active esters can then be prepared and these polypeptides can then be polymerized in the presence of a basic initiator by the method described above. The polymer obtained in this way has a regular distribution of the amino acids; its average molecular weight corresponds to the statistical number of polypeptides which have polymerized.

To obtain a regular polymer (I) of strictly defined molecular weight, it is possible to carry out a solid phase synthesis starting from the amino acids required for the preparation of the copolymer.

In the different steps of the preparation, the amino acid polymers are purified by the techniques of gel permeation chromatography and ultrafiltration, which enable the molecules to be separated according to their molecular weight. Gel permeation chromatography is performed according to the techniques described in Sci. Report of Toyo Soda, 1985, 29, (1) 37–54.

Ultrafiltration is performed on Amicon ® cells marketed by Amicon.

Gel permeation chromatography in association with refractometry is also used to determine the average molecular weight of the polymers according to the technique described by D. Lecacheux and R. Panaras in Carbohydrate Polymers, 1985, 5, 423–440. In this case, chromatography and then light scattering analysis are carried out on the copolymer and on reference substances with a known molecular weight, such as polyoxyethylenes, which are used in order to establish a calibration curve.

The average molecular weight (MW) is associated with a polydispersity index, which expresses the statistical distribution of the polymers of different molecular weights around the average molecular weight.

The cosmetic compositions according to the present invention contain, as active ingredient, from 0.1 to 10% and preferably from 0.5 to 5% by weight of an amino acid copolymer (I) or a mixture of at least two copolymers (I) as defined according to the present invention.

The copolymer or copolymers (I) are mixed with cosmetic excipients for the preparation of creams, lotions, emulsions or solutions.

To prepare cosmetic compositions, the components are mixed with the excipients generally employed in the art of cosmetics, such as, for example, fats of animal or vegetable origin, vegetable oils, fatty acids, alcohols, polyalkylene glycols, waxes, hydrocarbons and polyesters, and can be associated with water and with gelling agents if they are compatible. Other ingredients compatible with the components, such as preservatives like 4-hydroxybenzoic acid esters, antioxidants like butylhydroxytoluene or vitamin E derivatives, or fragrances, can be added to these preparations.

The fatty acids used as adjuvants in the cosmetic compositions of the present invention can be saturated or unsaturated, contain from 1 to 22 carbon atoms, be unsubstituted or substituted by a hydroxyl group and be in the free form or in the form of one of their alkali metal salts.

The cosmetic compositions according to the invention can be especially in the form of a cream in which the components are associated with excipients commonly used in cosmetology and compatible with said components, such as lanolin or derivatives thereof.

The cosmetic compositions of the invention can also take the form of a gel in appropriate excipients such as cellulose esters, acrylic polymers, methacrylic polymers, in particular polyglyceryl methacrylate, or other gelling agents.

The cosmetic compositions according to the invention can also take the form of a lotion, solution or microemulsion in which the components are dissolved or microdispersed.

The cosmetic compositions according to the invention can therefore be in the form of a microdispersion of components in a liquid containing water together with one or more surfactants. These dispersions have the characteristics of microemulsions and in practice have the appearance of true solutions.

These microemulsions have a good stability and can be kept for the necessary period of use at temperatures of between 0° and 60° C. without irreversible phase separation or sedimentation of the constituents. If needed, the compositions may be also prepared for immediate use.

The surfactants in the composition are selected from surface-active agents which may be used in cosmetology. Non-limiting examples which may be indicated are: sorbitol esters and polyethoxylated derivatives thereof, polyethoxylated (hydrogenated or non-hydrogenated) castor oils, ethylene oxide/propylene oxide block copolymers, polyethoxylated sterols and fatty alcohols, sodium laurylsulfate, sodium dioctylsulfosuccinate, egg or soya lecithins and polyethoxylated silicone oils.

According to the present invention, copolymers (I) can also be incorporated into biovectors such as liposomes or any other form which is suitable for cosmetic use and makes it possible to ensure an optimal selective tissue distribution.

The cosmetic compositions of the present invention are very well tolerated; they do not exhibit any phototoxicity and their application to the skin for prolonged periods of time does not produce any systemic effects.

The cosmetic compositions of the present invention are more particularly intended for:

improving the state of hydration of the skin, in a curative or preventive treatment, on skin which is dry, aged or burnt by the sun; and favoring tissue repair in skin which is aged or damaged by exogenous factors.

The moisturizing power of the copolymers (I) was studied on animals by applying methods similar to those described by D. Wilson et al. in Int. J. Cosmet. Sci., 1988, 10, 201–211.

Guinea-pigs of the HAIRLESS strain are used. The experiments are performed under stable conditions of temperature (22° C.±2) and relative humidity, and air movements are avoided.

To prepare the animals, two zones were delimited on the back of each guinea-pig:
a control zone on the left-hand side
a treated zone on the right-hand side All the guinea-pigs receive 0.2 ml of distilled water on the left zone and 0.2 ml of a 5% solution of copolymer (I) to be studied on the treated right zone.

The measurements are made using on the one hand a CM 420 corneometer and on the other hand an EP1 evaporimeter.

The CM 420 corneometer is manufactured by Schwarzhaupt and makes it possible to measure the moisturizing power of cosmetics. This instrument consists of a console and a probe for recording the conductance, the value of which is proportional to the water content. The measurement is obtained by applying the probe to the desired spot and observing the number displayed on the dial of the console.

The EP1 evaporimeter is marketed by Servo Med and makes it possible to measure the transepidermal water loss.

The rate of evaporation of water from the surface of the skin is measured by means of a method based on measurement of the gradient of water vapor pressure in the layer of air immediately adjacent to the skin. The instrument has a probe with humidity and temperature detectors. Measurement of the transepidermal water loss is made by applying the probe to the desired spot for thirty seconds. The transepidermal water loss measures not the water content of the stratum corneum but the rate at which the water diffuses towards the surface. This measurement provides an evaluation of the quality of the skin's natural barrier function.

To evaluate the moisturizing effect of the product, the animals were treated for 2 weeks.

Measurements and Treatment

For each animal, three measurements were made on each of the days corresponding to a treatment day.

The first measurement, $T_0$, is made every day before the animal is treated. Like the next measurements, this measurement was made on the treated zone and on the control zone. This determination on $D_0$ corresponds to the base value of the zone in question and enables the residual effect after 24 hours to be assessed on the following days.

The second measurement, $T_1$, is made thirty minutes after the treatment so as to eliminate any effect due to the water and so as to be able to assess the effect of the product just after its application.

The third measurement, $T_2$, is made four hours after the treatment so as to determine whether the product possesses a prolonged action.

The results obtained show that the compounds according to the invention cause a substantial and durable increase in skin hydration, measured by corneometry, which is accompanied in certain cases by a reduction in the transepidermal water losses (i.p.w.), measured by evaporimetry.

In conclusion, these products have a distinct moisturizing activity which persists for 24 hours The abbreviations below are used in the Examples and in the claims which follow:
TFA: trifluoroacetic acid
HBr: hydrobromic acid
OBzl: benzyl ester
ONp: p-nitrophenyl ester
Z: benzyloxycarbonyl
DMF: dimethylformamide
DCM: dichloromethane
OHBT: hydroxybenzotriazole
DCC: dicyclohexylcarbodiimide
DMSO: dimethylsulfoxide
DCU: dicyclohexylurea For the sake of simplification, some constituents of the cosmetic compositions have been designated by their tradename or by initials, the meanings of which are as follows:
Carbopol 940: carboxypolymethylene marketed by GOODRICH
EDTA: ethylenediaminotetraacetic acid
UVB filter: 2-ethylhexyl 4-methoxycinnamate (mark PARSOL MCX)

The non-limiting Examples which follow illustrate the preparation of the copolymers (I) and the cosmetic compositions according to the invention.

EXAMPLE 1

Glu-Lys (1/1) copolymer: SR 46512
A) Glu(OBzl)-Lys(Z) (1/1) copolymer 32 g of TFA.H-Lys(Z)-ONp and 29.32 g of TFA.H-Glu(OBzl)-ONp are dissolved in 200 ml of DMF. 200 ml of DCM are added. The medium is stirred and cooled to 5° C., 17.2 ml of triethylamine are added all at once and the mixture is then left to stand at room temperature for 4 days. The reaction medium is diluted with 100 ml of DMF, a further 1.72 ml of triethylamine are added and the mixture is then left to stand for 24 hours. The reaction mixture is then poured into 2 liters of vigorously stirred ethyl ether.

The precipitate obtained is filtered off and the solvent is driven off under vacuum until a constant weight of light yellow solid is obtained. M=25.92 g.

The product is used as such in the next step.
B) Hydrobromide of Glu-Lys (1/1) copolymer 15.8 g of the copolymer obtained in the previous step are dissolved in 150 ml of TFA. A stream of hydrogen bromide gas is passed into the medium for 30 minutes and the latter is then stirred at room temperature for 1 hour. The reaction medium is poured into 2 liters of ethyl ether at 0° C. After standing for 1 hour at 0° C., the precipitate formed is filtered off, washed copiously with ether and dried under vacuum in the presence of potassium hydroxide to give 12.90 g of the hydrobromide of Glu-Lys (1/1) copolymer.
C) Glu-Lys (1/1) copolymer The copolymer obtained in the previous step is dissolved in 500 ml of water and a pH of 1.2 is measured. 200 ml of Amberlite ® I.R. 45 resin are added. The pH of the medium is 7. It is stirred for 15 minutes and filtered. The filtrate is concentrated under vacuum at a temperature of between 30° and 35° C. and then lyophilized to give 7.35 g of a cream-colored pulverulent product.

The amino acid analysis is consistent with one lysine to one glutamic acid. The approximate molecular weight, MW, determined by the technique of gel permeation chromatography is 1440. Analysis of the NMR spectrum at 250 MHz confirms the absence of signals due to aromatic rings.

EXAMPLE 2

Pro-Glu (1/1) copolymer: SR 44478
A) Pro-Glu(OBzl) (1/1) copolymer 25.5 g of TFA.H-Pro-ONp and 34.39 g of TFA.H-Glu(OBzl)-ONp are dissolved in 160 ml of DMF. 160 ml of DCM are added. The medium is stirred and cooled to 5° C., 20.18 ml of triethylamine are added all at once and the mixture is then left to stand at room temperature for 5 days. A further 2 ml of triethylamine are added and the mixture is then left to stand for 48 hours. The reaction mixture is then concentrated to dryness under vacuum. The residue is dissolved in 500 ml of DCM and the solution is washed 3 times with 500 ml of a 5% aqueous solution of sodium bicarbonate and then with 500 ml of water. The organic phase is dried over magnesium sulfate and concentrated under vacuum at 30° C. until a constant weight of a yellow solid foam is obtained: 22.74 g. The product is used as such in the next step.

B) Pro-Glu (1/1) copolymer 22.74 g of the copolymer obtained in the previous step are dissolved in 300 ml of TFA. A stream of hydrogen bromide gas is passed into the medium for 60 minutes and the latter is then stirred at room temperature for 4 hours. The reaction mixture is poured into 2 liters of ethyl ether at 0° C. After standing for 1 hour at 0° C., the precipitate formed is filtered off, washed 3 times with 500 ml of ethyl ether and dried under vacuum in a desiccator in the presence of potassium hydroxide: 16.47 g. The product is dissolved in the amount of normal sodium hydroxide solution necessary for complete dissolution. The solution is purified by means of a dialysis tube against distilled water for 24 hours at room temperature. The product remaining in the dialysis tube is concentrated under vacuum at a temperature of between 30° and 35° C. and then lyophilized to give 10.36 g of a light yellow pulverulent product. This product is purified again by gel permeation chromatography on a column of Biogel® P 10, using a 2.5% by volume aqueous solution of acetic acid as the eluent, to give 9.80 g of a cream-colored pulverulent product. The amino acid analysis is consistent with 1 proline to 1 glutamic acid.

The approximate average molecular weight, MW, determined by the technique of gel permeation chromatography is 7600. Analysis of the NMR spectrum run at 250 MHz confirms the absence of signals due to aromatic rings.

EXAMPLE 3

Pro-Glu (1/1) copolymer: SR 44478
A) Pro-Glu (OBzl) (1/1) copolymer.

5 g of H-Pro-OH and 10.3 g of H-Glu (OBzl) —OH are suspended in 200 ml of DMSO. 6.62 ml of IFA are added; then, when all the products are dissolved, 11.92 ml of triethylamine, 17.71 g of DCC and 11.62 g of OHBT are added. The reaction is kept under stirring at room temperature for the night. Then 1.77 g of DCC are added and the reaction mixture is again kept under stirring for 24 hours. The DCU formed is filtered and the filtrate is poured into about 2 l of water with ice. The reaction mixture is twice extracted with 1 l of DCM; the organic solution is dried over magnesium sulfate and concentrated under vacuum at 50° C. until a constant weight of oil is obtained. This oil is dissolved in 100 ml of DCM and left to cool down to 0° C.

The second precipitate of DCU which is formed, is filtered and the filtrate is poured into 1 l of highly stirred hexane. The precipitate formed is filtered off, washed with hexane and dried.

8.6 g of cream-colored pulverulent product is obtained.

B) Pro-Glu (1/1) copolymer.

8 5 g of the copolymer obtained in the previous step are dissolved in 100 ml of TFA. A stream of hydrogen bromide gas is passed into the medium for 30 minutes and the latter is stirred at room temperature for 30 minutes. After standing for one hour at 0° C., the precipitate formed is filtered off, washed 3 times with 100 ml of ethyl ether, and dissolved in 200 ml of a saturated sodium bicarbonate aqueous solution; the resulting solution is dialysed for 24 hours against water in a dialyser AMICON provided with hollow-fiber cartridges (cutting thread: 2000). The dialysed solution is concentrated under vacuum at 50° C. until a constant weight of a solid light chestnut-colored foam is obtained: 6.6 g. The product is purified again by gel fermentation chromatography on a column PHARMACIA® K 50 containing FRACTOGEL® TSK HW 40 using water as eluent. Two fractions of a pulverulent product are obtained:

1) a fraction of 3.1 g of MW 6200 and a polydispersity index of 1.5;
2) a fraction of 1 g of M.W. 4000 and a polydispersity index of 1.5, measured by the technical gel permeation chromatography.

The amino acid analysis and the NMR at 250 MHz are consistent with 1 proline to 1 glutamic acid.

In the Examples of cosmetic compositions, COPOLYMER is understood as meaning a copolymer (I) or a mixture of 2 copolymers (I).

EXAMPLE 4

| MOISTURIZING GEL | |
|---|---|
| COPOLYMER | 3.00 g |
| Carbopol 940 | 0.20 g |
| Polyethylene glycol | 3.00 g |
| Preservatives | 0.50 g |
| Butylene glycol | 5.00 g |
| Ethoxylated sorbitan laurate | 0.50 g |
| Fragrance | 0.20 g |
| Triethanolamine | 0.25 g |
| Demineralized water | q.s. 100 g |

EXAMPLE 5

| FLUID MAKE-UP BASE | |
|---|---|
| COPOLYMER | 1.00 g |
| Ethoxylated soya sterols | 4.00 g |
| Soya sterols | 0.50 g |
| Glycerol monostearate | 1.00 g |
| Vegetable oil | 1.50 g |
| Ethylhexyl palmitate | 4.00 g |
| Cetyl alcohol | 0.50 g |
| Capric/caprylic triglycerides | 1.50 g |
| Silicone oil | 1.00 g |
| Mineral oil | 1.80 g |

-continued

| FLUID MAKE-UP BASE | |
|---|---|
| Lanolin alcohols | 0.20 g |
| Propylene glycol dipelargonate | 3.00 g |
| Lecithin | 1.00 g |
| Preservatives | 0.50 g |
| Butylene glycol | 5.00 g |
| Carbopol | 0.20 g |
| Triethanolamine | 0.20 g |
| EDTA tetrasodium salt | 0.10 g |
| Antioxidant | 0.01 g |
| Fragrance | 0.30 g |
| Demineralized water | q.s. 100 g |

EXAMPLE 6

| PROTECTIVE DAY CREAM | |
|---|---|
| COPOLYMER | 3.00 g |
| Ethoxylated sorbitan monostearate | 2.60 g |
| Silicone oil | 1.00 g |
| Cetyl alcohol | 2.00 g |
| Mineral oil | 3.00 g |
| Lanolin alcohol | 1.00 g |
| Perhydrosqualene | 1.00 g |
| Sorbitan monostearate | 2.40 g |
| Cetyl palmitate | 3.00 g |
| Isopropyl palmitate | 4.00 g |
| UVB filter | 2.00 g |
| EDTA tetrasodium salt | 0.10 g |
| Carbopol | 0.30 g |
| Triethanolamine | 0.30 g |
| Antioxidant | 0.01 g |
| Preservatives | 0.50 g |
| Fragrance | 0.30 g |
| Butylene glycol | 5.00 g |
| Demineralized water | q.s. 100 g |

EXAMPLE 7

| MOISTURIZING MICROEMULSIONS | |
|---|---|
| COPOLYMER | 5.00 g |
| Polyethylene glycol 600 hydroxystearate | 1.00 g |
| Polyethoxylated triglycerides (7-8 carbon atoms) | 0.25 g |
| Polyethylene glycol-7 glyceryl cocoate | 0.20 g |
| Dimethicone copolyol | 0.25 g |
| Propylene glycol | 12.50 g |
| Ethanol | 12.50 g |
| Carbopol | 0.40 g |
| Triethanolamine | 0.40 g |
| Fragrance | 0.30 g |
| Colorants | q.s. |
| Preservatives | 0.5 g |
| Demineralized water | q.s. 100 g |

EXAMPLE 8

| MOISTURIZING MAKE-UP FOUNDATION | |
|---|---|
| COPOLYMER | 2.00 g |
| EDTA tetrasodium salt | 0.10 g |
| Carboxymethyl cellulose | 0.20 g |
| Aluminum magnesium silicate | 1.00 g |
| Ethoxylated sorbitan laurate | 1.00 g |
| Propylene glycol | 5.00 g |
| Titanium oxide | 2.00 g |
| Talc | 1.00 g |
| Pigments | 1.00 g |
| Triethanolamine | 0.50 g |
| Preservatives | 0.50 g |
| Cetyl alcohol | 1.00 g |
| Lanolin alcohol | 3.00 g |
| Stearic acid | 1.80 g |

-continued

| MOISTURIZING MAKE-UP FOUNDATION | |
|---|---|
| Propylene glycol monostearate | 3.00 g |
| Isopropyl palmitate | 8.00 g |
| Vegetable oil | 2.00 g |
| Antioxidant | 0.05 g |
| Fragrance | 0.30 g |
| Demineralized water | q.s. 100 g |

EXAMPLE 9

| NIGHT CREAM | |
|---|---|
| COPOLYMER | 3.00 g |
| Cetyl alcohol | 2.00 g |
| Stearine | 2.50 g |
| Glycerol monostearate | 5.00 g |
| Isopropyl palmitate | 5.00 g |
| Vegetable oil | 3.00 g |
| Mineral oil | 2.00 g |
| Perhydrosqualene | 2.00 g |
| Silicone oil | 1.00 g |
| Karite butter | 2.00 g |
| 2-Ethylhexyl palmitate | 5.00 g |
| Triethanolamine | 5.50 g |
| Preservatives | 0.50 g |
| Butylene glycol | 5.00 g |
| EDTA tetrasodium salt | 0.30 g |
| Fragrance | 0.31 g |
| Antioxidant | 0.10 g |
| Demineralized water | q.s. 100 g |

EXAMPLE 10

| MOISTURIZING SERUM | |
|---|---|
| COPOLYMER | 5.00 g |
| Hydroxypropyl methyl cellulose | 0.30 g |
| Propylene glycol | 5.00 g |
| Glycerol | 5.00 g |
| Ethoxylated oleyl alcohol | 0.50 g |
| Fragrance | 0.30 g |
| EDTA tetrasodium salt | 0.10 g |
| Preservatives | 0.50 g |
| Bovine albumin | 5.00 g |
| Demineralized water | q.s. 100 g |

What is claimed is:

1. A method of moisturizing skin, comprising the step of applying to skin an effective moisturizing amount of an amino acid copolymer of the statistical formula $$\left\{A_m\left[NH-CH(-(CH_2)_a-COOH)-CO\right]_n B_p\left[NH-CH(-(CH_2)_b-COOH)-CO\right]_q\right\}_z \quad (I)$$

in which:
a and b are each independently 1 or 2;
A and B are similar or different and each is an amino acid selected from the group consisting of arginine, serine, proline, glycine, histidine, alanine, lysine, ornithine, citrulline, urocanic acid, asparagine and tyrosine;
m, n, p and q are integers such that the ratio $(n+q)/(m+p)$ is between 0.5 and 4; and
z is an integer such that the average molecular weight is between 1000 and 100,000; or a slat thereof.

2. A cosmetic composition which contains from 0.1 to 10% by weight of an amino acid copolymer or a mixture of 2 copolymers of the statistical formula

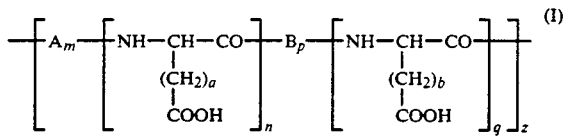

in which:
- a and b are each independently 1 or 2;
- A and B are similar or different and are in amino acid selected from the group consisting of arginine, serine, proline, glycine, histidine, alanine, lysine, ornithine, citrulline, urocanic acid, asparagine and tyrosine;
- m, n, p and q are integers such that the ratio $(n+q)/(m+p)$ is between 0.5 and 4; and
- z is an integer such that the average molecular weight is between 1000 and 100,000; or a salt thereof, and a pharmaceutically acceptable cosmetic excipient.

3. A cosmetic composition according to claim 2 which contains from 0.5 to 5% by weight of the amino acid copolymer or the mixture of 2 copolymers.

4. A cosmetic composition according to claim 2 which contains a mixture of 2 copolymers (I).

5. A cosmetic composition according to claim 2 wherein $a=b=2$ in the statistical formula of the copolymer (I).

6. A cosmetic composition according to claim 2 wherein $A=B$ in the statistical formula of the copolymer (I) and $(n+q)/(m+p)=1$.

7. A cosmetic composition according to claim 2 wherein the copolymer (I) is Lys-Glu (1/1).

8. A cosmetic composition according to claim 2 wherein the copolymer (I) is Pro-Glu (1/1).

9. A cosmetic composition according to claim 2 which contains a mixture of the 2 copolymers Pro-Glu (1/1) and Lys-Glu (1/1).

10. A cosmetic composition according to claim 2, wherein said pharmaceutically acceptable cosmetic excipient is one or more compounds selected from the group consisting of animal fats, vegetable fats, vegetable oils, fatty acids, alcohols, polyalkylene glycols, waxes, polyesters, gelling agents, preservatives, antioxidants, vitamin E derivatives and fragrances.

* * * * *

UNITED STATES PATENT AND TRADEMARK OFFICE
CERTIFICATE OF CORRECTION

PATENT NO. : 5,204,099
DATED : April 20, 1993
INVENTOR(S) : Alain BARBIER et al.

It is certified that error appears in the above-indentified patent and that said Letters Patent is hereby corrected as shown below:

Column 3, line 25, "100.000" should read --100,000--;
Column 6, line 6, insert a "." after "24 hours";
Column 7, line 63, "IFA" should read --TFA--;
Column 8, line 15, "85g" should read --8.5g--;
　　　　　　line 28, "fermentation" should read --permeation--;
　　　　　　line 34, "1.5" should read --1.5--;
　　　　　　line 35, "M.W." should read --MW--;
Column 10, line 68, "slat" should read --salt--;
Column 11, line 15, "in" should read --an--.

Signed and Sealed this

Sixth Day of September, 1994

Attest:

BRUCE LEHMAN

Attesting Officer　　Commissioner of Patents and Trademarks